(12) United States Patent
Feitisch et al.

(10) Patent No.: US 8,355,124 B2
(45) Date of Patent: Jan. 15, 2013

(54) ENERGY METER FOR MIXED STREAMS OF COMBUSTIBLE COMPOUNDS

(75) Inventors: Alfred Feitisch, Los Gatos, CA (US); Xiang Liu, Rancho Cucamonga, CA (US); Xin Zhou, Rancho Cucamonga, CA (US); Dale Langham, Katy, TX (US); Charles F. Cook, Humble, TX (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 13/301,707

(22) Filed: Nov. 21, 2011

(65) Prior Publication Data
US 2012/0064635 A1 Mar. 15, 2012

Related U.S. Application Data

(63) Continuation of application No. 12/181,239, filed on Jul. 28, 2008, now Pat. No. 8,064,052.

(60) Provisional application No. 60/952,540, filed on Jul. 27, 2007.

(51) Int. Cl.
*G01J 3/00* (2006.01)
(52) U.S. Cl. .................................... 356/300
(58) Field of Classification Search .................. 356/300
See application file for complete search history.

(56) References Cited

U.S. PATENT DOCUMENTS

| 5,790,420 A * | 8/1998 | Lang ........................... 700/287 |
| 6,941,230 B1 * | 9/2005 | Stirnberg et al. ............... 702/28 |
| 2010/0107729 A1 * | 5/2010 | Cline et al. ................... 73/23.37 |

* cited by examiner

*Primary Examiner* — Kara E Geisel
(74) *Attorney, Agent, or Firm* — Mintz, Levin, Cohn, Ferris, Glovsky and Popeo P.C.

(57) ABSTRACT

An energy content meter can spectroscopically quantify oxidation products after oxidation of a combustible mixture. The measured oxidation product concentrations or mole fractions can be converted to an energy content of the un-oxidized combustible mixture using a conversion factor that relates oxygen consumption during oxidation of the combustible mixture to the energy content of the combustible mixture.

20 Claims, 3 Drawing Sheets

ENERGY METER FOR MIXED STREAMS OF COMBUSTIBLE COMPOUNDS

CROSS-REFERENCE TO RELATED APPLICATIONS

This application is a continuation under 35 U.S.C. §120 U.S. patent application Ser. No. 12/181,239, filed on Jul. 28, 2008, now U.S. Pat. No. 8,064,052, which claims the benefit under 35 U.S.C. §119(e) of U.S. provisional patent application Ser. No. 60/952,540, filed on Jul. 27, 2007. The disclosure of each application listed in this paragraph is incorporated by reference herein in its entirety.

This application is related to co-pending and co-owned U.S. patent application Ser. No. 11/945,985, filed Nov. 27, 2007 and entitled "Energy Flow Measurement in Gas Pipelines" which is incorporated by reference herein in its entirety.

FIELD

The subject matter described herein relates to determination of the energy content of mixed composition gases.

BACKGROUND

Determining the energy content of mixtures containing hydrocarbons and other organic compounds can be important in a number of applications. Energy feedstocks, such as natural gas, liquid natural gas, crude and refined petroleum products, and the like may be valued and traded based on the energy content of the mixture. Even small offsets in the energy content (or BTU) value of the mixture can potentially translate to significant energy value differences. For example, in natural gas pipelines, very large quantities of hydrocarbon mixtures having variable composition are transported over very short periods. The energy density of natural gas is typically desirably maintained at or near 1050 BTU/ft$^3$ to ensure proper, energy efficient operation of turbines, furnaces, and other combustion systems and to reduce the potential for damage to equipment. Non-optimized operation can create excessive CO and $CO_2$, due to under efficient energy extraction and can also create costly damage to power generation turbines. Real time or near real-time BTU measurement of the turbine feeding gas stream is essential to prevent equipment damage and minimize emission of CO and $CO_2$.

Energy content measurements for a mixture can be performed with a calorimeter. For this technique, a mixture to be analyzed is fed to a calorimeter chamber at a known, constant rate to a jet at which the reaction occurs. Alternatively, a known volume of the mixture is analyzed in a batch manner. The reaction chamber and gas pipes are contained in a thermostatically controlled water bath to ensure constant temperature. The reaction is then started and the temperature rise measured after a known amount of gas has been fed into the reaction. Calibration of the calorimeter, either with a standard reaction or by electrical means, allows calculation of the enthalpy ($\Delta H$) of the reaction because the reaction is conducted at constant pressure. Flame calorimetry can be performed in near real time depending on the design of the device employed. However, if the heated mass has a large heat capacity, it will take longer to register a meaningful temperature shift which can result in a delay. Ambient heat loads can also introduce potential measurement delays and/or errors. In addition, calorimeter design is very difficult, especially for processes involving very small energy changes, e.g., energy changes on top of a large background such as pipeline gas. Maintenance and calibration of these devices can also require considerable resources.

Analyzers which calculate energy content by measuring residual oxygen left over from combustion of the gas provide indirect measurements that can also be susceptible to various errors. For example, oxygen can be consumed in the formation of nitrogen oxides from $N_2$ present in the mixture being tested, which can lead to over-estimation of the energy content. Furthermore, oxygen probes used in such sensors can be limited in their sensitivity and can have operating temperature limitations that could prevent their use in pyrolysis ovens. Cooling and further handling can also be required, thereby leading to additional analytical errors. Use of paramagnetic oxygen sensors can also limit the operating temperature and resolution. Incomplete oxidation of the mixture can lead to additional errors. The use of an oxygen stream for the oxidation can also lead to increased operating costs.

Sampling of the mixture composition by gas chromatography (GC) can be used to separate and quantify each species that is present. However, gas chromatography can have difficulty speciating compounds with 5 or 6 to 10 or more carbon atoms and can be susceptible to interference by contaminants such as water, sulfur compounds, and other mixture components that can foul the GC column. Additionally, GC measurements can take several minutes or even longer per sample. At pipeline pressures and transport speeds typical for natural gas, this delay can potentially lead to substantial billing errors, on the order of thousands of dollars. Gas chromatography also cannot determine the hydrogen concentration of a gas stream, so the total energy content can potentially be under-represented by such a measurement. Operation and maintenance costs of operating GCs can also be quite large due to the required consumable carrier gases and the regular maintenance required to assure that the instrument will continue to provide accurate data.

SUMMARY

In one aspect a method includes spectroscopically quantifying a measured concentration for each of one or more oxidation products created by oxidizing a sample volume of a mixture of combustible compounds, determining an oxygen consumption value for the sample volume of the mixture based on the measured concentrations of the one or more oxidation products in the sample volume, and converting the oxygen consumption value to an energy content for the mixture using a predetermined normalized energy content factor. The oxygen consumption value represents an amount of oxygen required to substantially oxidize the combustible compounds in the sample volume. The normalized energy content value is based on a relation between the oxygen consumption value and an enthalpy of combustion per mole fraction of the combustible compounds in the mixture.

In an interrelated aspect, a system includes a light source that generates a light beam or light pulses that are transmitted through a sample volume comprising one or more oxidation products formed by oxidation of one or more combustible compounds in a mixture, a detector that quantifies an intensity of the light beam or light pulses that are transmitted through the sample volume and that outputs a signal representative of the intensity of the light beam or light pulses that are transmitted through the sample volume, and a processor that receives the signal. The processor quantifies a measured concentration for each of the one or more oxidation products based on the signal, determines an oxygen consumption value for the sample volume of the mixture based on the measured concentrations of the one or more oxidation products in the sample volume, and converts the oxygen consumption value to an energy content for the mixture using a predetermined normalized energy content factor. The oxygen consumption value represents an amount of oxygen required to substantially oxidize the combustible compounds in the sample volume. The normalized energy content value includes a relation between the oxygen consumption value and an enthalpy of combustion per mole fraction of the combustible compounds in the mixture.

In optional variations, one or more of the following features can be included. The one or more combustible compounds in the sample volume of the mixture can be oxidized to produce the one or more oxidation products. This oxidizing can include providing an oxidizing reagent that includes at least one oxygen-containing compound to the sample volume. The oxidizing reagent can optionally be oxygen or air. The oxidizing reagent can be treated to reduce a background concentration of the one or more oxidation products prior to providing the oxidizing reagent. A first background concentration of the one or more oxidation products in the oxidizing reagent can be determined prior to providing the oxidizing reagent. The measured concentrations of the oxidation products in the sample volume can be reduced according to the first background concentration. A second background concentration of the one or more oxidation products in the sample volume of the mixture can be determined prior to oxidizing the combustible reagents. The measured concentrations of the oxidation products in the sample volume can be reduced according to the second background concentration. The oxidation products can include carbon dioxide and water. A concentration of one or more products of incomplete oxidation of the combustible compounds in the sample volume of the mixture can be quantified. The mixture can include natural gas.

The spectroscopically quantifying can include analyzing the concentration of the oxidation products using tunable diode laser spectroscopy at one or more wavelengths at which carbon dioxide and/or water vapor have measurable absorption features. Alternatively or in addition, the spectroscopically quantifying can include analyzing the concentration of the oxidation products using single or multiple line absorption spectroscopy at wavelengths at which carbon dioxide and/or water vapor have measurable absorption features. The spectroscopically quantifying can include generating a light beam or light pulses from a light source, directing the light beam or light pulses through a volume containing the one or more combustion products, and measuring the intensity of the light beam or light pulses exiting the volume. The measuring can include receiving the light beam or light pulses at a photodetector. The light beam or light pulses can include one or more wavelengths at which carbon dioxide and/or water vapor have measurable absorption features. The light source can include a tunable diode laser operated in either a scanned or fixed wavelength mode.

A system can further include an oxidation chamber that contains the sample volume during oxidation. The oxidation chamber can include a first inlet for the mixture and a second inlet for an oxidizing reagent. A spectroscopic analysis chamber can also be provided into which the one or more oxidation products are passed after oxidation of the combustible compounds in the sample volume in the oxidation chamber. The spectroscopic analysis chamber can include one or more windows via which the light beam or pulses pass through the sample volume to the detector. Alternatively, the oxidation chamber can further include one or more windows via which the light beam or pulses pass through the sample volume to the detector. A pre-treatment unit can also be included that reduces a background concentration of the one or more oxidation products in the oxidizing reagent prior to providing the oxidizing reagent. One or more valves can operate to periodically permit analysis of the oxidizing reagent to spectroscopically determine a first background concentration of the one or more oxidation products in the oxidizing reagent and wherein the processor subtracts the first background concentration from the measured concentrations of the oxidation products in the sample volume. One or more valves can operate to periodically permit analysis of the mixture to spectroscopically determine a second background concentration of the one or more oxidation products in the sample volume of the mixture prior to oxidizing the combustible reagents and wherein the processor subtracts the second background concentration from the measured concentrations of the oxidation products in the sample volume.

The subject matter described herein provides many advantages and benefits, including but not limited to real time energy measurement of mixed hydrocarbon and combustible mixtures and/or gas streams. Candidate mixtures and gas streams that can be analyzed include, but are not limited to, natural gas, gasoline, heating oil, diesel and others, regardless of composition. The contribution of hydrogen to the energy content of a gas can be measured as well, which can be an important benefit as hydrogen can potentially be a challenge to measure by gas chromatography or spectroscopic methods and systems. Direct, accurate, real time energy content measurements can reduce errors in billing and offsets in custody transfer of natural gas. Additionally, energy content measurements of combustible gases including natural gas, liquid natural gas, refinery fuel gas and other combustible fuels can allow for real time optimization of BTU content and combustion efficiency for energy generation, thereby reducing hazards to equipment from off-spec fuel and potentially reducing unnecessary green house gas emissions.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
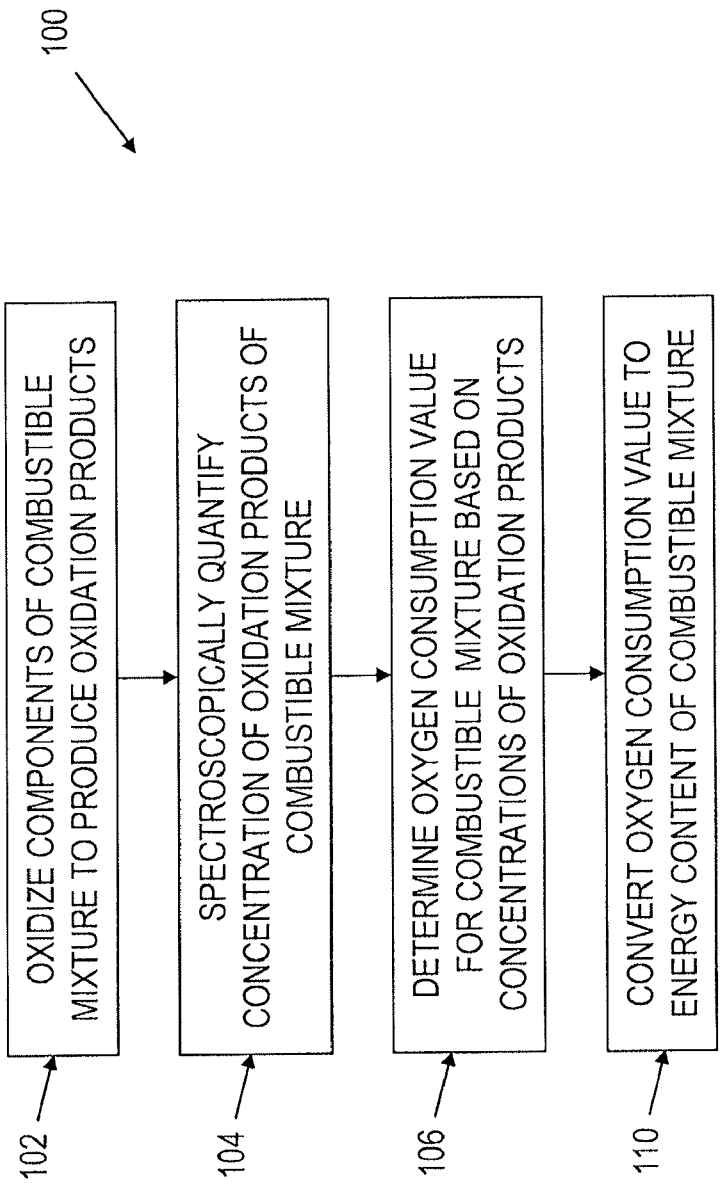
FIG. 1 is a process flow diagram illustrating a method for measuring the energy content of a combustible mixture.

The subject matter described herein includes methods, techniques, systems, structures, and articles of manufacture that may be used to enable measurement of the energy content of mixtures of combustible compounds, such as for example those containing hydrocarbons. These measurements can be performed quickly, in some examples in substantially real time. Such mixtures can include but are not limited to natural gas and its constituents, gasoline and its constituents, alkanes, alkenes, alkynes, alcohols, hydrogen, and mixtures thereof. Absorption spectroscopy is used in conjunction with an oxidation process to determine concentrations of $CO_2$ and $H_2O$, the primary end products of oxidation of the compounds in the mixture. Measurements can be conducted in real time at a wide range of temperatures, including but not limited to temperatures at which pyrolysis or catalyzed oxidation is conducted. In some implementations, direct tunable diode laser spectroscopic absorption techniques can be applied to quantify the molar concentration of carbon dioxide ($CO_2$) and water ($H_2O$) as end products of oxidation of a sample volume of the mixture. The oxidation can be performed in a suitable apparatus which allows complete or near-complete oxidation of the compounds in the sample volume, using air, oxygen, or some other suitable oxidizer. Combustion product concentrations, including but not necessarily limited to $CO_2$ and $H_2O$, can be determined with ppm level accuracy using the disclosed subject matter. The combustion product concentrations are then converted to an energy value for the combustible mixture.

Carbon monoxide (CO) can also be measured simultaneously, serially, or in parallel with $CO_2$ and $H_2O$ concentrations in the oxidized products using a spectroscopic technique to ensure a more accurate count of carbon atoms in the mixture being sampled even if oxidation does not proceed to completion in the pyrolysis or oxidation process. Likewise, residual hydrocarbons can also be measured in real time, near real time, or periodically to ascertain that combustion in the pyrolysis or oxidation process is proceeding efficiently and completely. These additional measurements can be performed via one or more spectroscopic or other techniques. Measurements of the oxidation product concentrations can be carried out directly at the high oxidation temperature if the pyrolysis or oxidation process is performed in a chamber or other vessel provided with windows that are transparent at the spectroscopic wavelengths being used for analysis. Alternatively, the spectroscopic measurements can be performed in a sample chamber or optical analysis cell that is arranged in series with a pyrolysis or oxidation chamber.

Comparison of chemical reaction equations for natural gas constituents with energy content tables published in the Gas Processors Association (GPA) report #2145-03 Rev. 1 indicates that complete oxidation of natural gas to $CO_2$ and $H_2O$ releases an approximate average energy of 2.5056 $BTU \cdot ft^{-3}$ per mole percent of the gas species per oxygen atom in the resultant stoichiometrically formed combustion products from the gas species. Table 1 lists energy contents for a variety of alkanes up to $C_{10}$. The values in the rightmost column of Table 1 are obtained by normalizing the GPA 2145-03 Rev. 1 values in the second column by the number of oxygen atoms required for complete oxidation of the gas species (which is equal to two times the number of $CO_2$ molecules plus the number of $H_2O$ molecules in the third column) and then by a 100% mole fraction for the pure gas species. In this manner, a robust estimate of the contribution of each combustible compound in a mixture to the total enthalpy of combustion of the mixture can be determined as a function of the mole fraction of the combustible compound in the mixture and the stoichiometric amount of oxygen required to fully oxidize the combustible compound. In mixtures, such as for example natural gas, that are composed largely of compounds with very similar normalized energy contents, the normalized energy content of the mixture can be estimated mathematically based on an expected composition of the combustible compounds in the mixture. Changes in the ratios of the combustible compounds in such mixtures typically have lower impact on the total energy content of the mixture than do the presence of non-combustible compounds in the mixture, such as for example nitrogen, water, carbon dioxide, noble gases, and the like. The current subject matter can account for the impact on the total energy content of a mixture that results from the presence of such compounds.

TABLE 1

Energy Content of Hydrocarbons.

| Gas Species | Energy Content, GPA 2145-03 Rev. 1 ($BTU \cdot ft^{-3}$) | Stoichiometric Products of full oxidation (per mole) | Normalized energy content ($BTU \cdot ft^{-3}$ per mole % per O atom |
|---|---|---|---|
| $CH_4$ | 1010.0 | $1CO_2 + 2H_2O$ | 2.525 |
| $C_2H_6$ | 1769.7 | $2CO_2 + 3H_2O$ | 2.528 |
| $C_3H_8$ | 2516.2 | $3CO_2 + 4H_2O$ | 2.516 |
| $i$-$C_4H_{10}$ | 3252.0 | $4CO_2 + 5H_2O$ | 2.5015 |
| $n$-$C_4H_{10}$ | 3262.4 | $4CO_2 + 5H_2O$ | 2.5095 |
| $i$-$C_5H_{12}$ | 4000.9 | $5CO_2 + 6H_2O$ | 2.5006 |
| $n$-$C_5H_{12}$ | 4008.7 | $5CO_2 + 6H_2O$ | 2.5054 |
| $n$-$C_6H_{14}$ | 4756.0 | $6CO_2 + 7H_2O$ | 2.5032 |
| $n$-$C_7H_{16}$ | 5502.5 | $7CO_2 + 8H_2O$ | 2.5011 |
| $n$-$C_8H_{18}$ | 6248.9 | $8CO_2 + 9H_2O$ | 2.4996 |
| $n$-$C_9H_{20}$ | 6996.4 | $9CO_2 + 10H_2O$ | 2.4987 |
| $n$-$C_{10}H_{22}$ | 7743.0 | $10CO_2 + 11H_2O$ | 2.4977 |
| Average | | | 2.5072 |

The average energy content per mole percent of the gas species per mole of oxygen atom consumption in oxidation for methane through $C_{10}$ alkanes is approximately 2.5072 $BTU \cdot ft^{-3}$ per mole percent of the gas species per oxygen atom with a range of about 1.9% of the average. Because $CO_2$ includes two moles of oxygen per mole of $CO_2$, one mole percent of $CO_2$ generated from oxidation and/or combustion of a mixture of methane to $C_{10}$ alkanes releases on average 5.014 $BTU \cdot ft^{-3}$ of energy and one mole percent of $H_2O$ generated releases 2.5072 $BTU \cdot ft^{-3}$ of energy, averaged over all $C_1$ through $C_{10}$ compounds. Note that these calculations are based on two moles of atomic oxygen per mole of $CO_2$ and one mole of atomic oxygen per mole of $H_2O$.

In an alternative implementation, the energy content per mole percent of the gas per oxygen atom consumed in oxidation for $C_1$ through $C_5$ alkanes can be averaged. The $C_1$ through $C_5$ alkanes include a majority of the components typically found in natural gas. The average energy content for $C_1$ through $C_5$ alkanes is approximately 2.5122 $BTU \cdot ft^{-3}$ per mole percent per oxygen atom necessary for complete oxidation. The range of energy content per mole percent per oxygen atom values for $C_1$ to $C_5$ alkanes is approximately 0.97% of the average value. Applying this average number to the products of a complete hydrocarbon oxidation process gives an energy content of 5.0245 $BTU \cdot ft^{-3}$ for each mole percent $CO_2$ and 2.5122 $BTU \cdot ft^{-3}$ for each mole percent $H_2O$ in the combustion products. In another alternative implementation, the methane energy value of 2.525 $BTU \cdot ft^{-3}$ per mole percent per oxygen atom can be used for natural gas using the assumption that approximately 70% to 90% of the mixture is methane.

Table 2 provides the results of further analysis in which the normalized energy content of methane through $C_{10}$ alkanes are compared to the average normalized energy content for $C_1$ to $C_5$ alkanes (third column) and to methane (fourth columns). As noted above, the average normalized energy content for $C_1$ to $C_5$ alkanes is approximately 2.5122 $BTU \cdot ft^{-3}$ per mole mole percent per oxygen atom, and the normalized energy content for methane is approximately 2.525 $BTU \cdot ft^{-3}$ per mole mole percent per oxygen atom. As Table 2 shows, deviation for the energy content contribution of the listed alkanes is in a range of less than about −0.63% to 0.58% when using the $C_1$ to $C_5$ average normalized energy content as representative of the entire mixture and in a range of about 0 to 1.09% when using the methane average normalized energy content as representative of the entire mixture.

Energy Contents of Hydrocarbons Relative to Methane Energy Content.

| Gas Species | Normalized energy content (BTU · ft$^{-3}$ per mole % per O atom) | Δ from C$_1$-C$_5$ average normalized energy content (BTU · ft$^{-3}$ per mole % per O atom) | Δ from methane normalized energy content (BTU · ft$^{-3}$ per mole % per O atom) |
|---|---|---|---|
| CH$_4$ | 2.525 | −0.51% | 0% |
| C$_2$H$_6$ | 2.528 | −0.63% | −0.12% |
| C$_3$H$_8$ | 2.516 | −0.15% | +0.36% |
| i-C$_4$H$_{10}$ | 2.5015 | +0.107% | +0.94% |
| n-C$_4$H$_{10}$ | 2.5095 | +0.11% | +0.62% |
| i-C$_5$H$_{12}$ | 2.5006 | +0.46% | +0.98% |
| n-C$_5$H$_{12}$ | 2.5054 | +0.27% | +0.78% |
| n-C$_6$H$_{14}$ | 2.5032 | +0.36% | +0.87% |
| n-C$_7$H$_{16}$ | 2.5011 | +0.44% | +0.96% |
| n-C$_8$H$_{18}$ | 2.4996 | +0.5% | +1.02% |
| n-C$_9$H$_{20}$ | 2.4987 | +0.54% | +1.05% |
| n-C$_{10}$H$_{22}$ | 2.4977 | +0.58% | +1.09% |
| Average CH4—C5H12 | 2.5122 | | |

FIG. 1 shows a process flow chart 100 illustrating a method for quantifying the energy content of a combustible mixture. At 102, the components of a combustible mixture can optionally be oxidized to produce oxidation products. Alternatively, the current subject matter can determine the concentrations of the oxidation products generated in an external oxidation process. The concentrations of the oxidation products are spectroscopically quantified at 104. The combustion products can include, but are not limited to, one or more of H$_2$O, CO$_2$, and CO. In one example, a tunable diode laser absorption spectrometer (TDLAS) can be used to measure the concentrations of one or more of the combustion products produced in an oxidation process that can be a pyrolysis process, combustion, catalytic oxidation, or the like.

An oxygen consumption value of the mixture is quantified at 106 based on the spectroscopically quantified oxidation product concentrations. In optional variations, the concentrations of incomplete oxidation products, such as for example carbon monoxide, alcohols, aldehydes, organic acids, and other partially oxidized or un-oxidized hydrocarbons, can also be quantified and used to adjust the observed oxidation product concentrations accordingly. In one example, the carbon monoxide concentration in the exhaust can be added to the carbon dioxide concentration using the assumption that in complete oxidation, carbon monoxide would become carbon dioxide. At 110 the oxygen consumption value is converted to an energy content of the combustible mixture or stream using a predetermined conversion factor. The predetermined conversion factor can optionally be determined as discussed above, or calculated based on one or more empirical or theoretical calculations.

Figure 2:
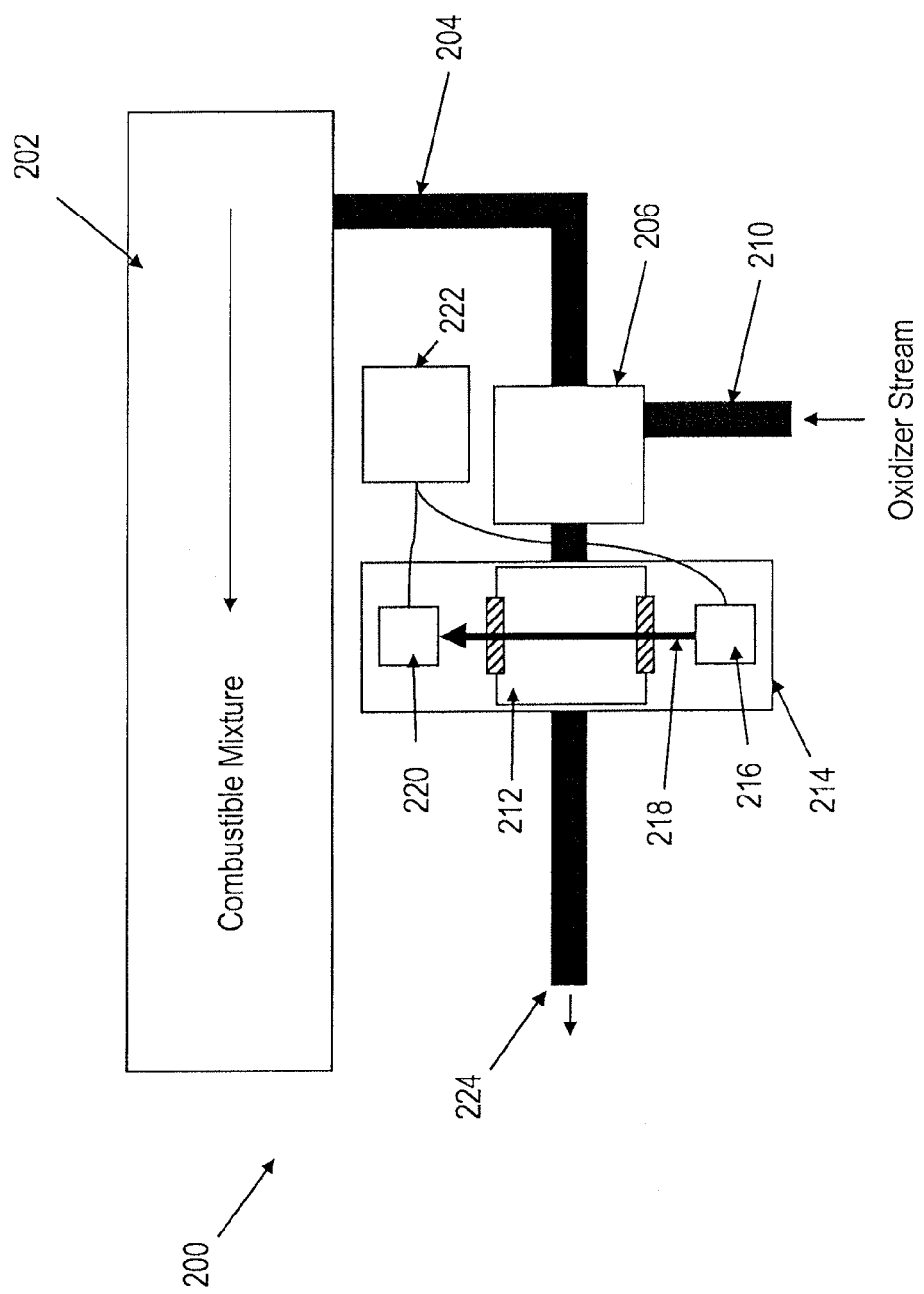
FIG. 2 is a schematic diagram illustrating a system for measuring the energy content of a combustible mixture.

FIG. 2 shows a schematic diagram 200 of an energy meter for a combustible mixture. The system depicted in FIG. 2 represents an example of a continuous or semi-continuous monitor that can be installed along a conduit carrying a flow stream of the combustible mixture. In some examples, the mixture can be natural gas flowing in a pipeline or other comparable conduit. Other types of mixtures and systems can also be analyzed for energy content using the current subject matter. For example, batch or continuous or semi-continuous flow measurements can be performed for mixtures extracted from a storage or holding tank or similar device or for combustible mixtures generated by industrial or commercial processes such as petroleum refining or manufacturing.

The combustible mixture can optionally be provided in a pipeline 202 as shown in FIG. 2. In other variations, the gas stream or mixture can be in a pressurized tank such as a transportation unit. The mixture is removed from the pipeline in FIG. 2 via an analyzer inlet 204 and conveyed to a pyrolysis or oxidation chamber 206 which can optionally contain a catalyst. Hydrocarbons and other combustible or oxidizable species in the mixture are oxidized in the pyrolysis or oxidation chamber 206 which ideally converts all carbon to carbon dioxide and all hydrogen to water vapor. As noted above, if incomplete oxidation occurs, the system can optionally also include functionality to quantify partial oxidation products such as carbon monoxide or other partially oxidized or unoxidized components of the combustible mixture. An oxidizer stream, which can optionally be air or oxygen gas or some other compound that is capable of providing oxygen to oxidize carbon-containing compounds, can be provided via an oxidizer inlet 210. In the example shown in FIG. 2, oxidation products are exhausted from the pyrolysis or oxidation chamber 206 to a sample chamber 212 that is part of an absorption spectrometer 214. A light source 216, that can be a laser such as a tunable diode laser, provides a light beam 218 that is projected through the gas contained in the sample chamber 212. One or more windows can be provided in the sample chamber 212 to allow the light beam to enter and exit the sample chamber 212. A mirror can optionally be provided to reflect the light beam and increase the effective path length within the sample chamber 212. Upon exiting the sample chamber 212, the light beam can impinge upon a detector 220 that can be a photodetector that quantifies the power or intensity of the light beam 218 after it has passed through the exhaust stream from the pyrolysis or oxidation chamber 206 and thereby provides a measurement of transmission and absorption of the light beam 218 by the combustion products in the sample chamber 212. The detector 220 can provide an output signal to a microprocessor or other controller 222 that converts the measured intensity of the transmitted light beam to concentrations of water vapor and carbon dioxide. The absorption spectrometer 214 can optionally be configured to determine the concentrations of one or more additional combustion products, such as for example carbon monoxide, alcohols, aldehydes, organic acids, and the like. The processor or other controller 222 can optionally also be coupled to the light source to control the generation of the light beam 218. The processor can further determine an energy content of the gas based on a predetermined conversion factor that relates atoms of oxygen required for complete combustion to the energy content of the gas. This conversion factor can be obtained as described above. Gas exits the sample chamber 212 via an outlet 224 that can optionally be vented to atmosphere.

Figure 3:
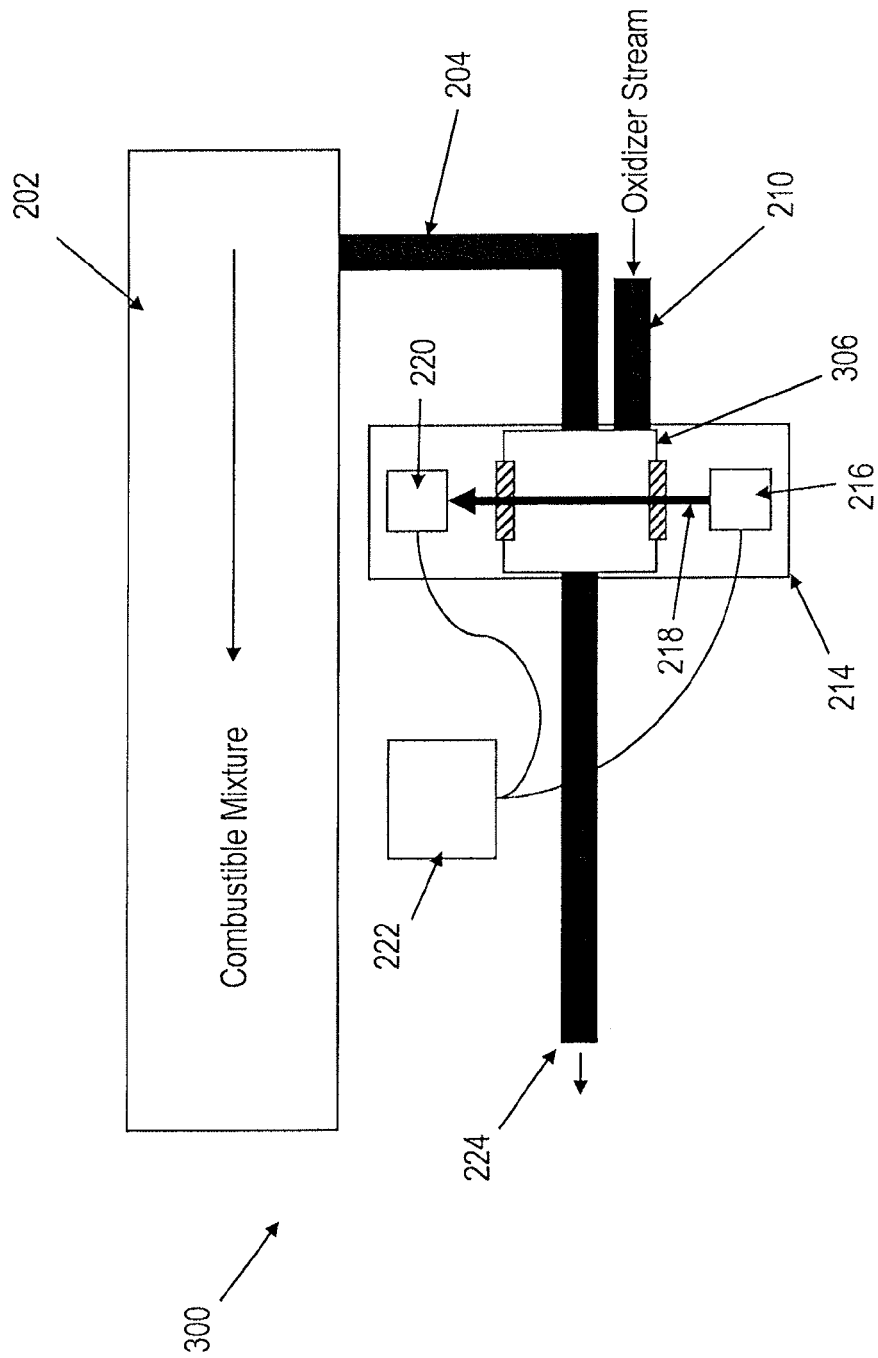
FIG. 3 is a schematic diagram illustrating a second system for measuring the energy content of a combustible mixture.

The example in FIG. 2 shows a separate sample chamber 212 and pyrolysis or oxidation chamber 206. In other variations, such as for example the system 300 shown in FIG. 3, a combination oxidation and spectroscopy chamber 306 can be provided with one or more windows to allow absorption spectroscopy to be performed on the oxidization products as they are formed by the oxidation process. The other components of the system 300 shown in FIG. 3 are similar to those in FIG. 2 and have the same reference numbers.

In one example, the absorption spectrometer 214 can be one or more tunable diode laser absorption spectrometers (TDLAS) operating at one or more wavelengths at which the combustion products have a strong absorption feature. The length of the path from the light source 216 can be selected based on the strength of the absorption line being employed.

In general, the stronger the absorbance, the shorter the path. For short paths, the light source 216 and the detector 220 can be placed at opposite ends of the absorption path. When the path needs to be longer the light source 216 and the detector 220 can be located at the same end of the path with a mirror at the opposite end. In this manner, the light traverses the "cell" length twice. When even longer cell are required, a Herriott cell, that allows the light to traverse between two concave spherical mirrors many times, can be employed. Herriott cells with path lengths of up to 100 m or greater can be employed in these types of measurements. Other types of optical cells that employ more complex technology can have effective path lengths of several thousand meters by causing a path length between the light source and the photodetector to traverse a sampled volume of gas many times.

In some implementations, a harmonic spectroscopy technique can be employed in connection with a TDL light source 216 to greatly improve the signal to noise ratio of the spectrometer 214. The TDL laser light source 216 wavelength can be modulated at a high frequency (kHz-MHz) and the detection of the signal can be performed at a multiple of the modulation frequency. If the detection is performed at twice the modulation frequency, the term second harmonic or "2f" spectroscopy is used. Advantages to this technique include the minimization of 1/f noise, and the removal of the sloping baseline that can be present on TDL spectra (due to the fact that the laser output power increases as the laser injection current increases, and changing the laser injection current is how the laser is tuned). In another implementation, direct absorption spectroscopy can be used. In this implementation, the frequency of the light source 216 in the spectrometer 214 can be tuned over a selected absorption transition and the zero-absorption baseline can be obtained by fitting the regions outside the absorption line to a low-order polynomial. The integrated absorbance is directly proportional to the concentrations of absorbing species in the path length as well as the line strength of the transition.

Typically, the mole fractions of carbon dioxide and water vapor in the exhaust from oxidation of a hydrocarbon mixture will be quite high, so the potentially improved sensitivity of harmonic spectroscopy may not be necessary. Other types of absorption spectroscopy that are capable of quantifying carbon dioxide and water vapor in a gas stream can also be used. Other light sources beside a tunable diode laser can also be used. For example a vertical cavity surface emission laser (VCSEL), quantum cascade lasers, horizontal cavity surface emitting lasers (HCSEL), tunable diode lasers that are tuned by either current or temperature adjustments or by adjustment of dispersive optical elements, including prisms and diffraction gratings, and the like. For tunable lasers, either direct lasing or harmonic frequency modulation techniques can be used as noted above. Broadband lasers can also be used. Tunable dye lasers, solid state lasers and color center lasers can also be used.

The detector 220 used can depend on the specific wavelengths of the light source and absorption lines to be measured. One possible detector is an indium gallium arsenide (InGaAs) photodiode sensitive to light in the 1200 to 2600 nm wavelength region. For longer wavelengths, an indium arsenide (InAs) photodiode, sensitive for wavelengths up to approximately 3.6 µm, can be used. Alternatively, indium antimonide (InSb) detectors are currently available for wavelengths as long as approximately 5.5 µm. Both of the indium devices operate in a photovoltaic mode and do not require a bias current for operation. These detectors, which lack low frequency noise, are advantageous for DC or low frequency applications. Such detectors are also advantageous for high speed pulse laser detection, making them particularly useful in trace gas absorption spectroscopy. Other detectors, such as for example silicon (Si), or germanium (Ge) photodiodes and mercury-cadmium-telluride (MCT) and lead-sulfide (PbS) detectors, can also be used.

The source of the oxidizing reagent for the oxidation reactions in the oxidation chamber 206 the combined oxidation and spectroscopy chamber 306 can optionally be dry oxygen from an oxygen source such as a tank or an oxygen generator. Alternatively, air can be used. If air is used as the oxygen source, the water vapor and/or the carbon dioxide content of the air provided to the chamber can optionally be measured so that the amount of reaction products observed after oxidation can be corrected for the concentrations prior to oxidation of the gas mixture or stream. Measurements of the water and/or carbon dioxide content of the incoming air stream can be done in a second spectroscopic absorption cell or alternatively in the same cell used to analyze the oxidation products. If the same sample chamber 212 is used, appropriate valving and plumbing can be provided to alternatively flow the gas stream being measured and the oxidizer steam through the sample chamber 212 to make sequential measurements of oxidation products and the water and/or carbon dioxide content of the oxidizer stream. An air drier can also optionally be included on the oxidizer stream to reduce the water vapor concentration prior to delivery of the air to the pyrolysis or oxidation chamber 206 or the combined oxidation and spectroscopy chamber 306. In some variations, the oxidizing reagent can be analyzed in parallel to measure a background baseline concentration for water vapor, carbon dioxide in the oxidizer stream.

Similarly, if the background concentrations of $CO_2$, $H_2O$, and/or other compounds containing oxygen such as alcohols, aldehydes, organic acids, and the like in the combustible mixture are non-negligible, the energy content measurement can potentially be influenced. $H_2O$, $CO_2$, and other oxygenated compounds in the combustible mixture can optionally be measured using a separate gas analyzer and/or by analyzing the un-oxidized combustible mixture prior to oxidation to determine the pre-oxidation concentrations of these gases. In some variations, the combustible mixture can be analyzed in parallel to the measurement of a $H_2O$ and/or $CO_2$ baseline in the combustible mixture.

In various implementations, a thermoelectric generator can be used as the pyrolysis or oxidation chamber 206 or as part of the combined oxidation and spectroscopy chamber 306. The thermoelectric generator can burn the gas mixture or stream to power the analyzer and provide an oxidized exhaust stream for analysis. One or more catalysts can be provided in the oxidation chamber 206 or the combined oxidation and spectroscopy chamber 306 to promote more efficient and complete oxidation and/or to enable lower temperature operation with complete or nearly complete oxidation of the combustible mixture.

The subject matter described herein may be embodied in systems, apparatus, methods, and/or articles depending on the desired configuration. In particular, aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

What is claimed is:

1. A method comprising:
spectroscopically quantifying a carbon dioxide concentration and a water concentration for a sample volume of combustion products produced in an oxidation process;
determining an oxygen consumption value for the sample volume based at least on the quantified carbon dioxide concentration and the quantified water concentration in the sample volume, the oxygen consumption value representing a number of moles of oxygen consumed to produce the quantified carbon dioxide concentration and the quantified water concentration from combustible compounds present in the sample volume prior to the oxidation process; and
converting the oxygen consumption value to an energy content for the sample volume, the converting comprising multiplying the oxygen consumption value by a normalized energy content factor, comprising an enthalpy of combustion per mole fraction of the combustible compounds in the mixture per mole of oxygen atoms consumed in the oxidation process.

2. A method as in claim 1, further comprising performing the oxidation process.

3. A method as in claim 2, wherein the performing of the oxidation process comprises providing an oxidizing reagent comprising at least one oxygen-containing compound to the sample volume.

4. A method as in claim 3, further comprising pre-treating the oxidizing reagent to reduce a background concentration of at least one of carbon dioxide and water prior to providing the oxidizing reagent.

5. A method as in claim 3, further comprising determining at least one of a first carbon dioxide background concentration and a first water background concentration in the oxidizing reagent prior to providing the oxidizing reagent; and
reducing at least one of the quantified carbon dioxide concentration and the quantified water concentration according to the at least one of the first carbon dioxide background concentration and the first water background concentration.

6. A method as in claim 3, further comprising determining at least one of a second carbon dioxide background concentration and a second water background concentration in the sample volume prior to providing the oxidizing reagent; and
reducing at least one of the quantified concentration of carbon dioxide and the quantified concentration of water according to the second carbon dioxide background concentration and the second water background concentration.

7. A method as in claim 1, further comprising quantifying a concentration of carbon monoxide in the sample volume; and wherein
the determining of the oxygen consumption value for the sample volume being further based on the quantified carbon monoxide concentration in the sample volume, the oxygen consumption value further representing a number of moles of oxygen consumed to produce the quantified carbon monoxide concentration in addition to the quantified carbon dioxide concentration and the quantified water concentration from the combustible compounds present in the sample volume prior to the oxidation process.

8. A method as in claim 1, wherein the spectroscopically quantifying comprises analyzing the concentration of carbon dioxide and oxygen using tunable diode laser spectroscopy at one or more wavelengths at which carbon dioxide and water vapor have measurable absorption features.

9. A method as in claim 1, wherein the spectroscopically quantifying comprises analyzing the concentration of carbon dioxide and oxygen using single or multiple line absorption spectroscopy at wavelengths at which carbon dioxide water vapor have measurable absorption features.

10. A method as in claim 1, wherein the spectroscopically quantifying comprises generating a light beam or light pulses from a light source, directing the light beam or light pulses through the sample volume, and measuring the intensity of the light beam or light pulses exiting the sample volume.

11. A method as in claim 10, wherein the light beam or light pulses comprise one or more wavelengths at which carbon dioxide and/or water vapor have measurable absorption features.

12. A method as in claim 10, wherein the light source comprises a tunable diode laser operated in a scanned or fixed wavelength mode.

13. A system comprising:
a light source that generates a light beam or light pulses that are transmitted through a sample of combustion products in an oxidation process;
a detector that quantifies an intensity of the light beam or light pulses that are transmitted through the sample volume and that outputs a signal representative of the intensity of the light beam or light pulses that are transmitted through the sample volume;
a processor that receives the signal, the processor performing operations comprising:
quantifying a carbon dioxide concentration and a water concentration for based on the signal;
determining an oxygen consumption value for the sample volume based at least on the quantified carbon dioxide concentration and the quantified water concentration in the sample volume, the oxygen consumption value representing a number of moles of oxygen consumed to produce the quantified carbon dioxide concentration and the quantified water concentration from combustible compounds present in the sample volume prior to the oxidation process; and
converting the oxygen consumption value to an energy content for the sample volume, the converting comprising multiplying the oxygen consumption value by a normalized energy content factor comprising an enthalpy of combustion per mole fraction of the combustible compounds per mole of oxygen atoms consumed in the oxidation process.

14. A system as in claim 13, further comprising an oxidation chamber that contains the sample volume during the oxidation process, the oxidation chamber comprising a first inlet for the sample volume and a second inlet for an oxidizing reagent.

15. A system as in claim 14, further comprising a spectroscopic analysis chamber into which the sample volume is passed after oxidation of the combustible compounds in the sample volume in the oxidation chamber, the spectroscopic analysis chamber comprising one or more windows via which the light beam or pulses pass through the sample volume to the detector.

16. A system as in claim 14, wherein the oxidation chamber further comprises one or more windows via which the light beam or pulses pass through the sample volume to the detector.

17. A system as in claim 14, further comprising a pretreatment unit that reduces at least one of a background carbon dioxide concentration, a background water concentration, and a background carbon monoxide concentration in the oxidizing reagent prior to providing the oxidizing reagent.

18. A system as in claim 14, further comprising one or more valves that operate to periodically permit analysis of the oxidizing reagent to spectroscopically determine at least one of a first background carbon dioxide concentration, a first background water concentration, and a first background carbon monoxide concentration in the oxidizing reagent and wherein the operations further comprise subtracting the at least one of the first background carbon dioxide concentration, the first background water concentration, and the first background carbon monoxide concentration, respectively from the quantified carbon dioxide concentration, the quantified water concentration, or a quantified carbon monoxide in the sample volume.

19. A system as in claim 14, further comprising one or more valves that operate to periodically permit analysis of the mixture to spectroscopically determine at least one of a second background carbon dioxide concentration, a second background water concentration, and a second background carbon monoxide concentration in the sample volume prior to providing the oxidizing reagent and wherein the operations further comprise subtracting the at least one of the second background carbon dioxide concentration, the second background water concentration, and the second background carbon monoxide concentration, respectively from the quantified carbon dioxide concentration, the quantified water concentration, or a quantified carbon monoxide in the sample volume.

20. A computer program product comprising a computer readable medium storing instructions that, when executed by a system comprising at least one processor, cause the system to perform operations comprising
  spectroscopically quantifying a carbon dioxide concentration and a water concentration for a sample volume of combustion products produced in an oxidation process;
  determining an oxygen consumption value for the sample volume based at least on the quantified carbon dioxide concentration and the quantified water concentration in the sample volume, the oxygen consumption value representing a number of moles of oxygen consumed to produce the quantified carbon dioxide concentration and the quantified water concentration from combustible compounds present in the sample volume prior to the oxidation process; and
  converting the oxygen consumption value to an energy content for the sample volume, the converting comprising multiplying the oxygen consumption value by a normalized energy content factor comprising an enthalpy of combustion per mole fraction of the combustible compounds per mole of oxygen atoms consumed in the oxidation process.

* * * * *